US011634485B2

(12) United States Patent
Corvari et al.

(10) Patent No.: US 11,634,485 B2
(45) Date of Patent: Apr. 25, 2023

(54) THERAPEUTIC ANTIBODY FORMULATION

(71) Applicant: Eli Lilly and Company, Indianapolis, IN (US)

(72) Inventors: Vincent John Corvari, Carmel, IN (US); Karthik Pisupati, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 307 days.

(21) Appl. No.: 16/787,254

(22) Filed: Feb. 11, 2020

(65) Prior Publication Data

US 2020/0262911 A1 Aug. 20, 2020

Related U.S. Application Data

(60) Provisional application No. 62/947,198, filed on Dec. 12, 2019, provisional application No. 62/880,846, filed on Jul. 31, 2019, provisional application No. 62/807,006, filed on Feb. 18, 2019.

(51) Int. Cl.
*A61K 39/395* (2006.01)
*C07K 16/24* (2006.01)
*A61K 47/26* (2006.01)
*A61K 9/08* (2006.01)
*A61K 9/00* (2006.01)
*A61K 39/00* (2006.01)

(52) U.S. Cl.
CPC .......... *C07K 16/244* (2013.01); *A61K 9/08* (2013.01); *A61K 47/26* (2013.01); *A61K 9/0019* (2013.01); *A61K 2039/505* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 6,884,879 B1 | 4/2005 | Baca et al. | |
| 7,291,132 B2 | 11/2007 | DeRuntz et al. | |
| 7,517,334 B2 | 4/2009 | Jacobs et al. | |
| 7,807,155 B2 | 10/2010 | Di Padova et al. | |
| 7,838,638 B2 | 11/2010 | Allan et al. | |
| 8,372,396 B2 | 2/2013 | Andya et al. | |
| 8,420,081 B2 | 4/2013 | Fraunhofer et al. | |
| 8,613,919 B1 | 12/2013 | Ma et al. | |
| 8,734,394 B2 | 5/2014 | Adams et al. | |
| 8,846,873 B2 | 9/2014 | Xiao et al. | |
| 8,961,964 B2 | 2/2015 | Liu et al. | |
| 9,345,661 B2 | 5/2016 | Adler et al. | |
| 9,376,491 B2 | 6/2016 | Corvari et al. | |
| 9,458,240 B2 | 10/2016 | Cosenza et al. | |
| 9,487,589 B2 | 11/2016 | Demeule et al. | |
| 9,700,485 B2 | 7/2017 | Weeks et al. | |
| 9,845,353 B2* | 12/2017 | Corvari | A61P 29/00 |
| 9,862,760 B2 | 1/2018 | Abend et al. | |
| 9,975,957 B2 | 5/2018 | Du et al. | |
| 9,982,032 B2 | 5/2018 | Park et al. | |
| 10,000,562 B2 | 6/2018 | Deshmukh et al. | |
| 10,472,416 B2* | 11/2019 | Corvari | A61P 35/00 |
| 2002/0045582 A1 | 4/2002 | Margolin et al. | |
| 2003/0113316 A1 | 6/2003 | Kaisheva et al. | |
| 2003/0215515 A1 | 11/2003 | Truong-Le et al. | |
| 2003/0219475 A1 | 11/2003 | Truong-Le | |
| 2004/0018200 A1 | 1/2004 | Oliver et al. | |
| 2004/0033228 A1 | 2/2004 | Krause et al. | |
| 2004/0035578 A1 | 2/2004 | Ross et al. | |
| 2004/0042972 A1 | 3/2004 | Truong-Le et al. | |
| 2004/0170623 A1 | 9/2004 | Arvinte et al. | |
| 2004/0191243 A1 | 9/2004 | Chen et al. | |
| 2004/0197324 A1 | 10/2004 | Liu et al. | |
| 2004/0208869 A1 | 10/2004 | Allan | |
| 2004/0241174 A1 | 12/2004 | Amphlett et al. | |
| 2004/0247588 A1 | 12/2004 | Johnson et al. | |
| 2005/0053666 A1 | 3/2005 | Tzannis et al. | |
| 2005/0095243 A1 | 5/2005 | Chan et al. | |
| 2005/0118163 A1 | 6/2005 | Mizushima et al. | |
| 2005/0136063 A1 | 6/2005 | Wang et al. | |
| 2005/0260204 A1 | 11/2005 | Allan | |
| 2006/0002942 A1 | 1/2006 | Kunz et al. | |
| 2006/0088523 A1 | 4/2006 | Andya et al. | |
| 2006/0193850 A1 | 8/2006 | Warne et al. | |
| 2006/0246060 A1 | 11/2006 | Nesta | |
| 2006/0286103 A1 | 12/2006 | Kolhe et al. | |
| 2007/0020255 A1 | 1/2007 | Ueno et al. | |

(Continued)

FOREIGN PATENT DOCUMENTS

AR 103622 2/2016
AU 2011226771 9/2011

(Continued)

OTHER PUBLICATIONS

Gokarn, Yatin R., Eva Kras, Carrie Nodgaard, Vasumathi Dharmavaram, R. Matthew Fesinmeyer, Heather Hultgen, Stephen Brych, Richard L. Remmele Jr, David N. Brems, and Susan Hershenson. "Self-buffering antibody formulations." *Journal of pharmaceutical sciences* 97, No. 8 (2008): 3051-3066.
Karow, Anne R., Sven Bahrenburg, and Patrick Garidel. "Buffer capacity of biologics—from buffer salts to buffering by antibodies." *Biotechnology progress* 29, No. 2 (2013): 480-492.
Piedmonte, Deirdre Murphy, and Michael J. Treuheit. "Formulation of Neulasta® (pegfilgrastim)." *Advanced drug delivery reviews* 60, No. 1 (2008): 50-58.
Stoner, Michael R., Norm Fischer, Lori Nixon, Scott Buckel, Mark Benke, Fred Austin, Theodore W. Randolph, and Brent S. Kendrick. "Protein-solute interactions affect the outcome of ultrafiltration/diafiltration operations." *Journal of pharmaceutical sciences* 93, No. 9 (2004): 2332-2342.

*Primary Examiner* — Yunsoo Kim
(74) *Attorney, Agent, or Firm* — Duane C. Marks

(57) ABSTRACT

Stable aqueous pharmaceutical formulations for therapeutic antibodies and methods of using such stable aqueous pharmaceutical formulations.

9 Claims, No Drawings
Specification includes a Sequence Listing.

(56) References Cited

U.S. PATENT DOCUMENTS

| | | |
|---|---|---|
| 2007/0031402 A1 | 2/2007 | Zhang et al. |
| 2007/0053871 A1 | 3/2007 | Li et al. |
| 2007/0086979 A1 | 4/2007 | Chevrier et al. |
| 2007/0110757 A1 | 5/2007 | Wei et al. |
| 2007/0110798 A1 | 5/2007 | Drummond et al. |
| 2007/0172479 A1 | 7/2007 | Warne et al. |
| 2007/0172520 A1 | 7/2007 | VanAuker et al. |
| 2007/0184050 A1 | 8/2007 | Ishikawa et al. |
| 2007/0196364 A1 | 8/2007 | Krishnamurthy et al. |
| 2007/0218064 A1 | 9/2007 | Benson et al. |
| 2007/0237758 A1 | 10/2007 | Barry et al. |
| 2008/0003220 A1 | 1/2008 | Gokarn |
| 2008/0071063 A1 | 3/2008 | Allan et al. |
| 2008/0112953 A1 | 5/2008 | McAuley et al. |
| 2008/0124326 A1 | 5/2008 | Rehder et al. |
| 2008/0152658 A1 | 6/2008 | Dagan et al. |
| 2008/0213282 A1 | 9/2008 | Jacob et al. |
| 2008/0311078 A1 | 12/2008 | Gokarn et al. |
| 2009/0060906 A1 | 3/2009 | Barry et al. |
| 2009/0148449 A1 | 6/2009 | De Weers et al. |
| 2009/0208492 A1 | 8/2009 | O'Connor et al. |
| 2009/0258017 A1 | 10/2009 | Callahan et al. |
| 2009/0263382 A1 | 10/2009 | Ewert et al. |
| 2009/0291062 A1 | 11/2009 | Fraunhofer et al. |
| 2009/0291076 A1 | 11/2009 | Morichika et al. |
| 2009/0306348 A1 | 12/2009 | Goldstein et al. |
| 2009/0324586 A1 | 12/2009 | Tchessalov et al. |
| 2010/0041870 A1 | 2/2010 | Tchessalov et al. |
| 2010/0074903 A1 | 3/2010 | Grauschopf et al. |
| 2010/0098712 A1 | 4/2010 | Adler et al. |
| 2010/0129379 A1 | 5/2010 | Carpenter et al. |
| 2010/0143331 A1 | 6/2010 | Schultz-Fademrecht et al. |
| 2010/0158919 A1 | 6/2010 | Dauphin et al. |
| 2010/0158925 A1 | 6/2010 | Agarkhed et al. |
| 2010/0172862 A1 | 7/2010 | Correia et al. |
| 2010/0189723 A1 | 7/2010 | Wagtmann et al. |
| 2010/0209434 A1 | 8/2010 | Bishop et al. |
| 2010/0226928 A1 | 9/2010 | Dani |
| 2010/0260766 A1 | 10/2010 | Srivastava et al. |
| 2010/0297117 A1 | 11/2010 | Sloey et al. |
| 2010/0303827 A1 | 12/2010 | Sharma, Sr. et al. |
| 2010/0322943 A1 | 12/2010 | Cantor |
| 2011/0014189 A1 | 1/2011 | Soula et al. |
| 2011/0014676 A1 | 1/2011 | Cowan et al. |
| 2011/0044977 A1 | 2/2011 | Adler et al. |
| 2011/0059079 A1 | 3/2011 | Babuka et al. |
| 2011/0070225 A1 | 3/2011 | Goldbach et al. |
| 2011/0076273 A1 | 3/2011 | Adler et al. |
| 2011/0158987 A1 | 6/2011 | Adler et al. |
| 2011/0171217 A1 | 7/2011 | Badkar et al. |
| 2011/0171241 A1 | 7/2011 | Dix et al. |
| 2011/0223208 A1 | 9/2011 | Hill et al. |
| 2011/0229490 A1 | 9/2011 | Li et al. |
| 2011/0236398 A1 | 9/2011 | Momm et al. |
| 2011/0256135 A1 | 10/2011 | Fraunhofer et al. |
| 2011/0256149 A1 | 10/2011 | Bishop et al. |
| 2011/0293605 A1 | 12/2011 | Sathish et al. |
| 2011/0300135 A1 | 12/2011 | Lobo et al. |
| 2011/0305639 A1 | 12/2011 | Lobo et al. |
| 2012/0009199 A1 | 1/2012 | Dimitrova et al. |
| 2012/0014968 A1 | 1/2012 | Walsh et al. |
| 2012/0027772 A1 | 2/2012 | Kabakoff et al. |
| 2012/0093839 A1 | 4/2012 | Brige et al. |
| 2012/0097565 A1 | 4/2012 | Dix et al. |
| 2012/0114646 A1 | 5/2012 | Tchessalov et al. |
| 2012/0121580 A1 | 5/2012 | Bhambhani et al. |
| 2012/0123688 A1 | 5/2012 | Ramasubramanyan et al. |
| 2012/0128687 A1 | 5/2012 | Adler et al. |
| 2012/0148576 A1 | 6/2012 | Sharma et al. |
| 2012/0164752 A1 | 6/2012 | Kano |
| 2012/0183531 A1 | 7/2012 | Lucas et al. |
| 2012/0231009 A1 | 9/2012 | Ramani et al. |
| 2012/0237532 A1 | 9/2012 | Olbrich et al. |
| 2012/0282249 A1 | 11/2012 | Fox et al. |
| 2012/0315285 A1 | 12/2012 | Momm et al. |
| 2013/0004484 A1 | 1/2013 | Demeule et al. |
| 2013/0022597 A1 | 1/2013 | Xiao et al. |
| 2013/0022621 A1 | 1/2013 | Liu et al. |
| 2013/0064825 A1 | 3/2013 | Chan et al. |
| 2013/0121991 A1 | 5/2013 | Huille et al. |
| 2013/0186797 A1 | 7/2013 | Walsh et al. |
| 2013/0189218 A1 | 7/2013 | Akullian et al. |
| 2013/0189277 A1 | 7/2013 | Walsh et al. |
| 2013/0202620 A1 | 8/2013 | Osslund |
| 2013/0209480 A1 | 8/2013 | Mpofu et al. |
| 2013/0216525 A1 | 8/2013 | Chen |
| 2013/0295082 A1 | 11/2013 | Garidel et al. |
| 2013/0309226 A1 | 11/2013 | Armstrong et al. |
| 2013/0323260 A1 | 12/2013 | Walsh et al. |
| 2013/0336968 A1 | 12/2013 | Danek-Bulius et al. |
| 2013/0344074 A1 | 12/2013 | Bender et al. |
| 2013/0344088 A1 | 12/2013 | Cosenza et al. |
| 2014/0004106 A1 | 1/2014 | Schnieders et al. |
| 2014/0004131 A1 | 1/2014 | Mueller et al. |
| 2014/0031769 A1 | 1/2014 | de Juan, Jr. et al. |
| 2014/0054883 A1 | 2/2014 | Lanigan et al. |
| 2014/0065158 A1 | 3/2014 | Ma et al. |
| 2014/0120086 A1 | 5/2014 | Rast et al. |
| 2014/0161817 A1 | 6/2014 | Siedler et al. |
| 2014/0186373 A1 | 7/2014 | Cosenza et al. |
| 2014/0219956 A1 | 8/2014 | Govindan et al. |
| 2014/0227250 A1 | 8/2014 | Li et al. |
| 2014/0234296 A1 | 8/2014 | Sharma et al. |
| 2014/0271636 A1 | 9/2014 | Rast et al. |
| 2014/0271659 A1 | 9/2014 | Ma et al. |
| 2014/0286969 A1 | 9/2014 | Tschoepe et al. |
| 2014/0314748 A1 | 10/2014 | Gokarn et al. |
| 2014/0335084 A1 | 11/2014 | Fast et al. |
| 2014/0341885 A1 | 11/2014 | Diluzio et al. |
| 2014/0348855 A1 | 11/2014 | Deshmukh et al. |
| 2014/0348856 A1 | 11/2014 | Hsieh et al. |
| 2015/0071920 A1 | 3/2015 | Larson et al. |
| 2015/0071936 A1 | 3/2015 | Mendiratta et al. |
| 2015/0079074 A1 | 3/2015 | Garidel et al. |
| 2015/0118249 A1 | 4/2015 | Leach et al. |
| 2015/0147337 A1 | 5/2015 | Reichert et al. |
| 2015/0150982 A1 | 6/2015 | Michael et al. |
| 2015/0165064 A1 | 6/2015 | Bregeon et al. |
| 2015/0209430 A1 | 7/2015 | Benedict et al. |
| 2015/0225479 A1 | 8/2015 | Huille et al. |
| 2015/0239970 A1 | 8/2015 | Bee et al. |
| 2015/0259419 A1 | 9/2015 | Liu et al. |
| 2015/0274819 A1 | 10/2015 | Gwee |
| 2015/0291689 A1 | 10/2015 | Padley et al. |
| 2015/0307606 A1 | 10/2015 | Basarkar et al. |
| 2015/0307617 A1 | 10/2015 | Du et al. |
| 2015/0329628 A1 | 11/2015 | Antochshuk et al. |
| 2015/0329632 A1 | 11/2015 | Kashi et al. |
| 2015/0342888 A1 | 12/2015 | Rast et al. |
| 2015/0343058 A1 | 12/2015 | Albanese et al. |
| 2015/0344558 A1 | 12/2015 | Smith |
| 2016/0000916 A1 | 1/2016 | Crotts et al. |
| 2016/0025749 A1 | 1/2016 | Park et al. |
| 2016/0045615 A1 | 2/2016 | Li et al. |
| 2016/0075777 A1 | 3/2016 | Carayon et al. |
| 2016/0128944 A1 | 5/2016 | Chawrai et al. |
| 2016/0130337 A1 | 5/2016 | Gekkieva et al. |
| 2016/0137727 A1 | 5/2016 | Le et al. |
| 2016/0144025 A1 | 5/2016 | Vitti et al. |
| 2016/0279258 A1 | 9/2016 | Valbjorn et al. |
| 2016/0304599 A1* | 10/2016 | Manning ............... A61K 47/22 |
| 2016/0304607 A1 | 10/2016 | Sadineni et al. |
| 2016/0319022 A1 | 11/2016 | Yang et al. |
| 2016/0376342 A1 | 12/2016 | Park et al. |
| 2017/0015732 A1 | 1/2017 | Park et al. |
| 2017/0022248 A1 | 1/2017 | Son et al. |
| 2017/0028062 A1 | 2/2017 | Amsberry et al. |
| 2017/0051066 A1 | 2/2017 | Depaz et al. |
| 2017/0066823 A1 | 3/2017 | Edwards et al. |
| 2017/0088605 A1 | 3/2017 | Abend et al. |
| 2017/0106090 A1 | 4/2017 | Gadgil et al. |
| 2017/0137535 A1 | 5/2017 | Petry et al. |
| 2017/0174772 A1 | 6/2017 | Nirula et al. |
| 2017/0209582 A1 | 7/2017 | Park et al. |

(56) References Cited

U.S. PATENT DOCUMENTS

| | | |
|---|---|---|
| 2017/0218092 A1 | 8/2017 | Chiu et al. |
| 2017/0233467 A1 | 8/2017 | Lu et al. |
| 2017/0240617 A1 | 8/2017 | Sloan et al. |
| 2017/0247460 A1 | 8/2017 | Geiger et al. |
| 2017/0273909 A1 | 9/2017 | Mathiowitz et al. |
| 2017/0274076 A1 | 9/2017 | Hay et al. |
| 2017/0281769 A1 | 10/2017 | Eriksson et al. |
| 2017/0360929 A1 | 12/2017 | Sinha et al. |
| 2017/0360951 A1 | 12/2017 | Deonarain et al. |
| 2017/0368174 A1 | 12/2017 | Joerg et al. |
| 2018/0000932 A1 | 1/2018 | Bansal |
| 2018/0000933 A1 | 1/2018 | Ingram et al. |
| 2018/0008707 A1 | 1/2018 | Bussemer et al. |
| 2018/0028652 A1 | 2/2018 | Boonen et al. |
| 2018/0066046 A1 | 3/2018 | Smith |
| 2018/0099049 A1 | 4/2018 | Tang et al. |
| 2018/0153988 A1 | 6/2018 | Demopulos et al. |
| 2018/0201673 A1 | 7/2018 | Linnik |
| 2018/0243439 A1 | 8/2018 | Horiuchi et al. |
| 2018/0251526 A1 | 9/2018 | Lobo et al. |
| 2018/0289802 A1 | 10/2018 | Banks et al. |
| 2018/0296470 A1 | 10/2018 | Eng-Wong et al. |
| 2018/0325728 A1 | 11/2018 | Weikart et al. |
| 2018/0333493 A1 | 11/2018 | Shenoy |
| 2018/0339045 A1 | 11/2018 | Li et al. |
| 2018/0369377 A1 | 12/2018 | Rinaldi et al. |
| 2019/0016817 A1 | 1/2019 | Taddei et al. |
| 2019/0030123 A1 | 1/2019 | Sigl |
| 2019/0030180 A1 | 1/2019 | Harlow et al. |
| 2019/0040137 A1 | 2/2019 | Hu et al. |
| 2019/0046641 A1 | 2/2019 | Patel et al. |
| 2019/0060241 A1 | 2/2019 | Patel et al. |
| 2019/0083617 A1 | 3/2019 | Yates et al. |
| 2019/0099489 A1 | 4/2019 | Mackay |
| 2019/0125661 A1 | 5/2019 | Al Kobaisi et al. |
| 2019/0134196 A1 | 5/2019 | Zhang et al. |
| 2019/0194311 A1 | 6/2019 | Fasth et al. |
| 2019/0255173 A1 | 8/2019 | Francis et al. |
| 2019/0284282 A1 | 9/2019 | Jayaraman et al. |
| 2019/0300615 A1 | 10/2019 | Yang et al. |
| 2019/0322742 A1 | 10/2019 | Garidel et al. |
| 2019/0336586 A1 | 11/2019 | Yasukawa et al. |
| 2019/0343918 A1 | 11/2019 | Graham et al. |
| 2019/0343956 A1 | 11/2019 | Lee et al. |
| 2019/0358324 A1 | 11/2019 | Tang et al. |
| 2019/0359709 A1 | 11/2019 | Tang et al. |
| 2019/0367636 A1 | 12/2019 | Olbrich et al. |
| 2020/0016267 A1 | 1/2020 | Rinaldi et al. |
| 2020/0023061 A1 | 1/2020 | Jezek et al. |
| 2020/0023062 A1 | 1/2020 | Jezek et al. |
| 2020/0024363 A1 | 1/2020 | Teran et al. |
| 2020/0032163 A1 | 1/2020 | Bouchez et al. |
| 2020/0048346 A1 | 2/2020 | Yates et al. |
| 2020/0055938 A1 | 2/2020 | Desai et al. |
| 2020/0093927 A1 | 3/2020 | Kaya et al. |
| 2020/0131251 A1 | 4/2020 | Mhalasakant et al. |
| 2020/0147213 A1 | 5/2020 | Sharma et al. |
| 2020/0155678 A1 | 5/2020 | Chen et al. |
| 2020/0199209 A1 | 6/2020 | Fang et al. |
| 2020/0206350 A1 | 7/2020 | Chu et al. |
| 2020/0216524 A1 | 7/2020 | Cady et al. |
| 2020/0231698 A1 | 7/2020 | Fast et al. |
| 2020/0253875 A1 | 8/2020 | Coffman et al. |
| 2020/0262911 A1 | 8/2020 | Corvari et al. |
| 2020/0268675 A1 | 8/2020 | Varum et al. |
| 2020/0283516 A1 | 9/2020 | Lobo et al. |
| 2020/0297845 A1 | 9/2020 | Hu et al. |
| 2020/0317771 A1 | 10/2020 | Chevrier et al. |
| 2020/0323772 A1 | 10/2020 | Jones et al. |
| 2020/0354463 A1 | 11/2020 | Brych et al. |
| 2020/0362023 A1 | 11/2020 | Soto et al. |
| 2020/0390699 A1 | 12/2020 | Solfato et al. |
| 2020/0390705 A1 | 12/2020 | Batens et al. |
| 2020/0392224 A1 | 12/2020 | Soubrane et al. |
| 2020/0399391 A1 | 12/2020 | Chiron Blondel et al. |
| 2021/0000743 A1 | 1/2021 | Lee et al. |
| 2021/0002369 A1 | 1/2021 | Ahmed et al. |
| 2021/0030868 A1 | 2/2021 | Huang et al. |
| 2021/0047407 A1 | 2/2021 | Christian et al. |
| 2021/0054079 A1 | 2/2021 | Biddlecombe et al. |
| 2021/0070869 A1 | 3/2021 | Janmaat et al. |
| 2021/0087250 A1 | 3/2021 | Werle et al. |
| 2021/0101974 A1 | 4/2021 | Zhang |
| 2021/0106683 A1 | 4/2021 | Durran et al. |

FOREIGN PATENT DOCUMENTS

| Country | Number | Date |
|---|---|---|
| CN | 106474470 A | 3/2017 |
| CN | 106620690 A | 5/2017 |
| CN | 107400164 A | 11/2017 |
| CN | 109745559 A | 5/2019 |
| CN | 110124030 A | 8/2019 |
| CN | 110538321 A | 12/2019 |
| CN | 111840217 A | 10/2020 |
| DO | P2005000210 A | 4/2006 |
| EP | 3766481 A | 1/2021 |
| IN | 00185CH2012 A | 1/2014 |
| JP | 2010241718 A2 | 10/2010 |
| JP | 2017184730 A2 | 10/2017 |
| JP | 2019073463 A2 | 5/2019 |
| TW | 201836637 A | 10/2018 |
| WO | 2004039337 A2 | 5/2004 |
| WO | 2005065709 A2 | 7/2005 |
| WO | 2008029908 A1 | 3/2008 |
| WO | 2009015345 A1 | 1/2009 |
| WO | 2009120684 A1 | 10/2009 |
| WO | 2010148321 A1 | 12/2010 |
| WO | 2011029892 A2 | 3/2011 |
| WO | 2011141926 A2 | 11/2011 |
| WO | 2012028683 A1 | 3/2012 |
| WO | 2015110930 A1 | 7/2015 |
| WO | 2016036678 A1 | 3/2016 |
| WO | 2017051273 A1 | 3/2017 |
| WO | 2017055966 A1 | 4/2017 |
| WO | 2017149513 A1 | 9/2017 |
| WO | 2017208210 A1 | 12/2017 |
| WO | 2017214187 A1 | 12/2017 |
| WO | 2018122053 A1 | 7/2018 |
| WO | 2018169348 A1 | 9/2018 |
| WO | 2018179138 A1 | 10/2018 |
| WO | 2019011719 A1 | 1/2019 |
| WO | 2019018640 A1 | 1/2019 |
| WO | 2019039483 A1 | 2/2019 |
| WO | 2019105450 A1 | 2/2019 |
| WO | 2019120269 A1 | 6/2019 |
| WO | 2020233540 A1 | 8/2019 |
| WO | 2019197428 A1 | 10/2019 |
| WO | 2019204380 A1 | 10/2019 |
| WO | 2019220204 A2 | 11/2019 |
| WO | 2019232478 A1 | 12/2019 |
| WO | 2019236435 A1 | 12/2019 |
| WO | 2019245373 A1 | 12/2019 |
| WO | 2019246271 A1 | 12/2019 |
| WO | 2019246312 A1 | 12/2019 |
| WO | 2019246313 A1 | 12/2019 |
| WO | 2019246317 A1 | 12/2019 |
| WO | 2019246455 A1 | 12/2019 |
| WO | 2021058005 A1 | 12/2019 |
| WO | 2020004368 A1 | 1/2020 |
| WO | 2020006722 A1 | 1/2020 |
| WO | 2020008361 A1 | 1/2020 |
| WO | 2020016417 A1 | 1/2020 |
| WO | 2020017901 A1 | 1/2020 |
| WO | 2020041532 A1 | 2/2020 |
| WO | 2020053301 A1 | 3/2020 |
| WO | 2020053321 A1 | 3/2020 |
| WO | 2020072896 A1 | 4/2020 |
| WO | 2020073345 A1 | 4/2020 |
| WO | 2020075746 A1 | 4/2020 |
| WO | 2020081408 A1 | 4/2020 |
| WO | 2020087003 A1 | 4/2020 |
| WO | 2020088346 A1 | 5/2020 |
| WO | 2020089051 A1 | 5/2020 |
| WO | 2020094744 A1 | 5/2020 |

(56) References Cited

FOREIGN PATENT DOCUMENTS

| | | |
|---|---|---|
| WO | 2020097141 A1 | 5/2020 |
| WO | 2020117373 A1 | 6/2020 |
| WO | 2020120730 A1 | 6/2020 |
| WO | 2020154704 A2 | 7/2020 |
| WO | 2020215021 A1 | 7/2020 |
| WO | 2020155017 A1 | 8/2020 |
| WO | 2020160323 A2 | 8/2020 |
| WO | 2020192693 A1 | 9/2020 |
| WO | 2020205716 A1 | 10/2020 |
| WO | 2020223565 A1 | 11/2020 |
| WO | 2020233534 A1 | 11/2020 |
| WO | 2020243346 A1 | 12/2020 |
| WO | 2020247572 A1 | 12/2020 |
| WO | 2020257998 A1 | 12/2020 |
| WO | 2021013689 A1 | 1/2021 |
| WO | 2021050953 A1 | 3/2021 |
| WO | 2021053591 A1 | 3/2021 |
| WO | 2021067820 A1 | 4/2021 |

* cited by examiner

THERAPEUTIC ANTIBODY FORMULATION

REFERENCE TO AN ELECTRONIC SEQUENCE LISTING

The instant application contains a Sequence Listing which has been submitted electronically in ASCII format and is hereby incorporated by reference in its entirety. Said ASCII copy, created on Oct. 4, 2022, is named X22251 REPLACEMENTSEQUENCELISTING10042022 and is 9,529 bytes in size.

The present invention is in the field of medicine. More particularly, the present invention relates to aqueous pharmaceutical formulations comprising therapeutic antibodies that are suitable for subcutaneous ("SQ"), intramuscular ("IM"), and/or intraperitoneal ("IP") administration.

Administration of therapeutic antibodies via SQ, IP and/or IM administration is both common and advantageous. Such routes of administration allow the therapeutic antibody to be delivered in a short period of time and allow patients to self-administer therapeutic antibodies without visiting a medical practitioner. However, formulating therapeutic antibodies into aqueous pharmaceutical formulations suitable for SQ, IM and/or IP administration is both challenging and unpredictable. Additionally, undesirable injection-associated pain, even after a syringe needle is removed, has been reported with such routes of administration and can impair patient compliance with therapy.

The challenge and unpredictability associated with formulating therapeutic antibodies into aqueous pharmaceutical formulations suitable for SQ, IM and/or IP administration is due, in part, to the numerous properties a pharmaceutical formulation must possess to be therapeutically viable. Aqueous pharmaceutical formulations must provide stability to the therapeutic antibody in solution while, at the same time, maintaining the therapeutic antibody's functional characteristics essential for therapeutic efficacy such as target affinity, selectivity and potency. In addition, the aqueous pharmaceutical formulation must also be safe for administration to, and well tolerated by, patients as well as being suitable for manufacturing and storage.

Formulating high concentrations of therapeutic antibodies is even more complex. For example, increased rates of antibody degradation, cleavage, clipping, high molecular weight aggregation, dimerization, trimerization, precipitation pH shift, turbidity, solution color change, changes in charge, isomerization, oxidation and/or deamination (all of which affect the therapeutic antibody concentration, functionality and efficacy) have been reported for aqueous formulations of highly concentrated therapeutic antibodies. Another known challenge when formulating high concentrations of therapeutic antibodies is an increase in viscosity which can negatively affect SQ, IM and/or IP administration of an aqueous pharmaceutical formulation. Additionally, injection-associated pain has been reported with formulations having increased viscosity.

Furthermore, some therapeutic antibodies such as ixekizumab possess charge distributions leading to high levels of intermolecular interactions (e.g., as may be shown by Dynamic Light Scattering), phase separation, gelation and precipitation, making solubility of the molecule in aqueous solution, especially at high concentrations, very challenging to balance. Charge distribution of such antibodies may also manifest in an isoelectric point preventing formulation at neutral pH. For example, some therapeutic antibodies have a polarity, or dipole moment, such that they are only stable in aqueous formulations within narrow, non-neutral, pH windows. Injection-associated pain has been reported, however, for acidic (e.g., <pH 6.5) pharmaceutical formulations of therapeutic antibodies. Thus, such therapeutic antibodies, such as ixekizumab which possesses an isoelectric point of 8.1 (requiring acidic pH formulation), pose additional, unpredictable challenges for formulating in a way that balances stability of the therapeutic antibody with functional properties required for efficacy, as well as tolerability by patients.

Ixekizumab is a highly specific anti-IL17A antagonistic antibody, as described, for example, in U.S. Pat. No. 7,838,638. Commercially marketed under the tradename TALTZ®, ixekizumab is administered subcutaneously to patients in a highly concentrated (about 80 mg/mL) pharmaceutical formulation having an acidic pH (about 5.7). The commercial pharmaceutical formulation of ixekizumab, as described in U.S. Pat. No. 9,376,491, also includes high concentrations of citrate buffer (about 20 mM) and NaCl (about 200 mM). However, pharmaceutical formulations having acidic pH and high concentrations of NaCl and/or citrate buffer have been associated with injection-associated pain and patients have reported injection-associated pain after injecting the commercial pharmaceutical formulation of ixekizumab.

Injection-associated pain of aqueous pharmaceutical formulations comprising therapeutic antibodies is a complex, multifactorial issue. For example, each individual component, and/or concentration, ratio and characteristic thereof, of an aqueous pharmaceutical formulation can impact injection-associated pain associated with a therapeutic. Likewise, individual components (and/or concentrations, ratios and characteristics thereof) can impact the stability, functional characteristics, manufacturability and/or tolerability of a formulated therapeutic antibody in an aqueous pharmaceutical formulation. Thus, while a specific formulation adjustment may provide a beneficial impact to a given aspect of the formulation, the same adjustment may also negatively impact other aspects of the formulation. Even further adding to the complexity, a nearly limitless number of different formulation components (e.g., buffers and excipients), as well as concentrations and ratios thereof, have been reported. However, there remains little-to-no correlation for predicting the impact of a specific formulation on the various properties and characteristics of a given therapeutic antibody.

Accordingly, there is a need for an aqueous pharmaceutical formulation of therapeutic antibodies suitable for SQ, IM and/or IP administration and which is well tolerated by patients, exhibiting a therapeutically beneficial level of injection-associated pain. More particularly, there is a need for such aqueous pharmaceutical formulation for highly concentrated therapeutic antibodies possessing an isoelectric point not compatible with neutral pH in solution, requiring aqueous formulation at an acidic pH. Even more particularly, there is a need for an aqueous pharmaceutical formulation of ixekizumab suitable for SQ, IM and/or IP administration and which is well tolerated by patients, exhibiting an improved level of injection-associated pain over the commercial pharmaceutical formulation of ixekizumab (as described in U.S. Pat. No. 9,376,491). Such aqueous pharmaceutical formulation must also provide stability for the therapeutic antibody and preserve the properties of the therapeutic antibody essential for therapeutic efficacy. Such aqueous pharmaceutical formulations must also be amendable to manufacturing, preferably having an extended shelf life.

The aqueous pharmaceutical formulations provided herein satisfy the aforementioned needs in a surprising and unexpected way. More particularly, the aqueous pharmaceutical formulations provided herein are bufferless aqueous pharmaceutical formulations, suitable for SQ, IM and/or IP administration of high concentrations of ixekizumab, while also preserving the functional characteristics of ixekizumab essential for therapeutic efficacy. Additionally, the aqueous pharmaceutical formulations provided herein are well tolerated by patients, exhibiting an improved level of injection-associated pain over the commercial pharmaceutical formulation of ixekizumab and providing a therapeutically favorable level of injection-associated pain.

Accordingly, the present disclosure provides a bufferless, aqueous pharmaceutical formulation for administering SQ, IM or IP a high concentration of a therapeutic antibody to a patient with a therapeutically favorable level of injection-associated pain, the aqueous pharmaceutical formulation comprising a therapeutic antibody at a concentration of greater than 50 mg/mL, 60 mg/mL, 70 mg/mL, 80 mg/mL, 90 mg/mL, 100 mg/mL, 110 mg/mL or 120 mg/mL; sucrose in a concentration of 234 mM+/−10%; and a surfactant in a concentration between 0.005% w/v+/−10% to 0.05% w/v+/−10%, wherein, the pharmaceutical formulation is an aqueous solution at a pH between 5.2 to 6.5. According to specific embodiments, the surfactant is polysorbate 20 or polysorbate 80. In further specific embodiments, the surfactant is polysorbate 80. According to some embodiments, the bufferless aqueous pharmaceutical formulation is substantially free of an ionic tonicity excipient. In some embodiments, the pharmaceutical formulation is substantially free of L-amino acid excipients. In further embodiments, the antibody possesses an isoelectric point not compatible with neutral pH in solution. In some such embodiments, the antibody possesses an isoelectric point of ≥7.5 and in even further embodiments, the antibody possesses an isoelectric point of ≥8.0. In further, specific embodiments of the aqueous pharmaceutical formulations provided herein, the therapeutic antibody is an anti-IL-17A antibody comprising a LCVR having the amino acid sequence of SEQ ID NO.7 and a HCVR having the amino acid sequence of SEQ ID NO.8. In even further specific embodiments, the anti-IL17A antibody comprises a light chain (LC) having the amino acid sequence of SEQ ID NO.9 and a heavy chain (HC) having the amino acid sequence of SEQ ID NO.10. According to embodiments of the present disclosure, an aqueous pharmaceutical formulation of the present disclosure is provided, wherein the aqueous pharmaceutical formulation upon SQ, IP and/or IM administration to a patient exhibits a reduced risk of, and/or a, therapeutically favorable level of injection-associated pain.

According to particular embodiments of the present disclosure, a bufferless aqueous pharmaceutical formulation for an anti-IL1A antibody is provided. In embodiments, the anti-IL1A antibody comprises a light chain variable region (LCVR) comprising complementarity determining regions (CDRs) LCDR1, LCDR2, and LCDR3 and a heavy chain variable region (HCVR) comprising CDRs HCDR1, HCDR2, and HCDR3, wherein LCDR1 has the amino acid sequence of SEQ ID NO.1, LCDR2 has the amino acid sequence of SEQ ID NO.2, LCDR3 has the amino acid sequence of SEQ ID NO.3, HCDR1 has the amino acid sequence of SEQ ID NO.4, HCDR2 has the amino acid sequence of SEQ ID NO.5, and HCDR3 has the amino acid sequence of SEQ ID NO.6. According to such embodiments, the aqueous pharmaceutical formulation is an aqueous solution at a pH of between 5.2 to 6.5, and comprises the anti-IL17A antibody in a concentration of greater than 60 mg/mL+/−10%, 70 mg/mL+/−10%, 80 mg/mL+/−10%, 88 mg/mL+/−10%, 100 mg/mL+/−10%, 120 mg/mL+/−10% or 160 mg/mL+/−10%; sucrose in a concentration of 234 mM+/−10%; and a surfactant in a concentration of 0.005+/−10% to 0.05+/−10% % w/v. According to some embodiments, the bufferless aqueous pharmaceutical formulation is substantially free of an ionic tonicity excipient. In some embodiments, the pharmaceutical formulation is substantially free of L-amino acid excipients. In some embodiments, the surfactant is one of polysorbate 20 or 80. In more specific embodiments, the surfactant is polysorbate 80. In even more specific embodiments, the polysorbate 80 is at a concentration of 0.03% w/v+/−10%. According to such embodiments, the bufferless aqueous pharmaceutical formulation is suitable for SQ, IP and/or IM administration to a patient and exhibits an improved level of injection-associated pain over the commercial pharmaceutical formulation of ixekizumab and/or provides a therapeutically favorable level of injection-associated pain.

In particular embodiments, the aqueous pharmaceutical formulations provided herein comprise an antibody in a concentration of about 80 mg/mL (e.g., +/−10%); sucrose in a concentration of about 234 mM (e.g., +/−10%); and polysorbate 80 in a concentration of about 0.03% w/v (e.g., +/−10%), and the pharmaceutical formulation is substantially free of an ionic tonicity excipient, substantially free of L-amino acid excipients, and is at a pH of about 5.7 (e.g., +/−10%), and the antibody is an anti-IL17A antibody comprising a LCVR having the amino acid sequence of SEQ ID NO.7 and a HCVR having the amino acid sequence of SEQ ID NO.8. In further such embodiments, the anti-IL17A antibody comprising a heavy chain having the amino acid sequence of SEQ ID NO. 10 and a light chain having the amino acid sequence of SEQ ID NO. 9. According to such embodiments, the aqueous pharmaceutical formulation is suitable for SQ, IP and/or IM administration to a patient and exhibits an improved level of injection-associated pain over the commercial pharmaceutical formulation of ixekizumab and/or provides a therapeutically favorable level of injection-associated pain.

In further embodiments, a system for subcutaneously delivering an aqueous pharmaceutical formulation to a patient in need of treatment is provided. Such system includes a device having a chamber, a drive mechanism operatively coupled to the chamber, and a needle, the chamber being capable of storing a liquid, the needle having a bore in fluid communication with an outlet of the chamber to receive a liquid from the chamber, and the drive mechanism being operative to force the transfer of a liquid from the chamber into the bore of the needle. Such system also includes a pharmaceutical formulation of the present disclosure disposed within the chamber and the inner wall of the chamber having a silicone oil coating at an amount of less than about 0.4 mg. According to some more specific embodiments, the inner wall of the chamber has a silicone oil coating at an amount of about 0.2 mg or an amount of less than about 0.2 mg. According to some embodiments of the system, the patient is in need of treatment of RA, Ps, GenPs, Pruritus, AS, PA, PPP, HS or MM.

In further embodiments, the present disclosure provides a method for reducing injection-associated pain and/or providing a therapeutically favorable level of injection-associated pain experienced by a patient at the time of, or shortly after, SQ, IM and/or IP injection of an aqueous pharmaceutical formulation comprising a therapeutic antibody, the method comprising administering to a patient an aqueous pharmaceutical formulation of the present disclosure. According to embodiments, the present disclosure provides a method of delivering a therapeutic antibody to a patient with a therapeutically favorable level of injection-associated pain, wherein the method comprises administering to a patient a pharmaceutical formulation of the present disclosure, wherein the method provides a therapeutically favorable level of injection-associated pain. According to further embodiments, the present disclosure provides an improved method of delivering a therapeutic antibody to a patient, wherein the improvement comprises a reduction in, and/or providing a therapeutically favorable level of, injection-associated pain with SQ, IM or IP administration of an aqueous pharmaceutical formulation, the method comprising administering to a patient an aqueous pharmaceutical formulation of the present disclosure. According to embodiments, the reduction in injection-associated pain comprises a reduction from commercially available formulations and/or providing a therapeutically favorable level of injection-associated pain. According to embodiments, a therapeutically favorable level of injection-associated pain may comprise a VAS score of less than 30 mm or a VAS score of less than 20 mm.

According to embodiments, the present disclosure provides an improved method for administering an anti-IL17A antibody to a patient in need thereof, wherein the improvement comprises a reduction in the level of injection-associated pain upon the administration of a SQ, IM or IP injection of an aqueous pharmaceutical formulation, the method comprising administering to the patient an aqueous pharmaceutical formulation of the present disclosure, wherein said step of administering provides an improved level of injection-associated pain and/or provides a therapeutically favorable level of injection-associated pain. According to some embodiments, the aqueous pharmaceutical formulation consists essentially of an aqueous pharmaceutical formulation of the present disclosure. According to embodiments, the reduction in the level of injection-associated pain comprises providing an improved level of injection-associated pain (for example, a reduction in VAS score compared to the commercial formulation of ixekizumab, i.e., the citrate and NaCl formulation exemplified by the control formulation of Table 2).

According to some embodiments, the method provides a therapeutically favorable level of injection-associated pain comprising a VAS score of less than 30 mm or less than 20 mm. According to embodiments, the anti-IL17A antibody is ixekizumab and, according to some such embodiments, the improved level of injection-associated pain comprises a reduction in VAS score compared to the commercial formulation of ixekizumab (the citrate and NaCl formulation exemplified by the control formulation of Table 2). According to some embodiments, the aqueous pharmaceutical formulation is administered by SQ injection.

According to further embodiments of the present disclosure, an improved method of treating at least one of PsO, PsA and AxSpa is provided, wherein the improvement comprises a reduction in injection-associated pain upon the SQ administration of an aqueous pharmaceutical formulation comprising an anti-IL17A antibody, the method comprising administering an aqueous pharmaceutical formulation of the present disclosure, wherein said step of administering provides an improved level of injection-associated pain and/or provides a therapeutically favorable level of injection-associated pain. According to some embodiments, a therapeutically favorable level of injection-associated pain is provided comprising a VAS score of less than 30 mm or less than 20 mm. In some more specific embodiments, the anti-IL17A antibody is ixekizumab and, according to some such embodiments, the improved level of injection-associated pain comprises a reduction in VAS score compared to the commercial formulation of ixekizumab (the citrate and NaCl formulation exemplified by the control formulation of Table 2).

The present disclosure also provides an aqueous pharmaceutical formulation of the present disclosure for use in therapy. In particular embodiments, the present disclosure provides an aqueous pharmaceutical formulation of the present disclosure for use in the treatment of rheumatoid arthritis (RA), psoriasis (Ps), genital psoriasis (GenPs), pruritus, ankylosing spondylitis (AS), psoriatic arthritis (PA), palmoplantar pustulosis (PPP), Hidradenitis suppurativa (HS) or multiple myeloma (MM). According to further embodiments of the present disclosure, a use of an aqueous pharmaceutical formulation of the present disclosure for the manufacturer of a medicament for the treatment of RA, Ps, GenPs, pruritus, AS, PA, PPP, HS or MM is provided. According to such embodiments, use of such aqueous pharmaceutical formulations is suitable for SQ, IP and/or IM administration to a patient and exhibits an improved level of injection-associated pain over the commercial pharmaceutical formulation of ixekizumab and/or provides a therapeutically favorable level of injection-associated pain.

According to particular embodiments, the present disclosure provides a method of treating RA, Ps, GenPs, pruritus, AS, PA, PPP, HS or MM comprising administering to a patient in need thereof an effective amount of an aqueous pharmaceutical formulation of the present disclosure, wherein the aqueous pharmaceutical formulation comprises an anti-IL17A antibody. In a more particular embodiment, such method of treating includes administering subcutaneously, to the patient, an initial dose of the aqueous pharmaceutical formulation, on day 0, followed by administering subcutaneously the aqueous pharmaceutical formulation to the patient at every four week interval thereafter, wherein the aqueous pharmaceutical formulation administered to the patient at every four week interval after the initial dose comprises the anti-IL17A antibody at a concentration of about 80 mg/mL. In another particular embodiment, such method of treating includes administering subcutaneously, to the patient, an initial dose of the aqueous pharmaceutical formulation, on day 0, followed by administering subcutaneously the aqueous pharmaceutical formulation to the patient at every two week interval thereafter, wherein the aqueous pharmaceutical formulation administered to the patient at every two week interval after the initial dose comprises the anti-IL17A antibody at a concentration of about 80 mg/mL. In yet another particular embodiment, such method of treating includes administering subcutaneously, to the patient, an initial dose of the aqueous pharmaceutical formulation, on day 0, followed by administering subcutaneously the aqueous pharmaceutical formulation to the patient on each of days 14, 28, 42, 56, 70 and 84, and followed by administering subcutaneously the aqueous pharmaceutical formulation to the patient at every four week interval thereafter, wherein the aqueous pharmaceutical formulation, administered to the patient at each of days 14, 28, 42, 56, 70 and 84, and every four week interval thereafter, comprises the anti-IL17A antibody at a concentration of about 80 mg/mL. According to some of the methods of treating provided by the instant disclosure, the initial dose of the aqueous pharmaceutical formulation comprises about 160 mg of the anti-IL17A antibody. In some such embodiments, the about 160 mg initial dose of the aqueous pharmaceutical formulation comprises two doses of the aqueous pharmaceutical formulation, each dose comprising about 80 mg of the anti-IL17A antibody. According to such methods, the aqueous pharmaceutical formulation exhibits an improved level of injection-associated pain over the commercial pharmaceutical formulation of ixekizumab and/or provides a therapeutically favorable level of injection-associated pain.

According to particular embodiments, there is provided herein an aqueous pharmaceutical formulation comprising an anti-IL17A antibody for use in the treatment of RA, Ps, GenPs, pruritus, AS, PA, PPP, HS or MM wherein the pharmaceutical formulation is to be administered subcutaneously with an initial dose on day 0, followed by a dose every four weeks interval thereafter, wherein the pharmaceutical formulation to be administered at every four week interval after the initial dose comprises the anti-IL17A antibody at a concentration of about 80 mg/mL. In another particular embodiment, there is provided pharmaceutical formulations disclosed herein comprising an anti-IL17A antibody for use in the treatment of RA, Ps, GenPs, pruritus, AS, PA, PPP, HS or MM wherein the pharmaceutical formulation is to be administered subcutaneously with an initial dose on day 0, followed by a dose every two weeks interval thereafter, wherein the pharmaceutical formulation to be administered at every two week interval after the initial dose comprises the anti-IL17A antibody at a concentration of about 80 mg/mL. In yet another particular embodiment, there is provided pharmaceutical formulations disclosed herein comprising an anti-IL17A antibody for use in the treatment of RA, Ps, GenPs, pruritus, AS, PA, PPP, HS or MM wherein the pharmaceutical formulation is to be administered subcutaneously with an initial dose on day 0, followed by a dose on each of days 14, 28, 42, 56, 70 and 84, wherein the pharmaceutical formulation to be administered on each of days 14, 28, 42, 56, 70 and 84 after the initial dose comprises the anti-IL17A antibody at a concentration of about 80 mg/mL. According to some embodiments, the initial dose of the aqueous pharmaceutical formulation comprises about 160 mg of the anti-IL17A antibody. In some such embodiments, the about 160 mg initial dose of the aqueous pharmaceutical formulation comprises two doses of the aqueous pharmaceutical formulation, each dose comprising about 80 mg of the anti-IL17A antibody. According to such embodiments, the aqueous pharmaceutical formulations provided herein exhibit an improved level of injection-associated pain over the commercial pharmaceutical formulation of ixekizumab and/or provide a therapeutically favorable level of injection-associated pain.

As used interchangeably herein, the expressions "aqueous pharmaceutical formulation" or "pharmaceutical formulation" mean an aqueous solution having at least one therapeutic antibody capable of exerting a biological effect in a human, at least one inactive ingredient (e.g., excipient, surfactant, etc.) which, when combined with the therapeutic antibody, is suitable for therapeutic administration to a human. The pharmaceutical formulations provided by the present disclosure are bufferless (i.e., do not comprise agents such as citrate buffer, histidine buffer, acetate buffer, or the like, or combinations thereof, which have acid-base conjugate components, for resisting pH change), aqueous, stable formulations wherein the degree of degradation, modification, aggregation, loss of biological activity and the like, of therapeutic antibodies therein, is acceptably controlled and does not increase unacceptably with time.

As used herein, the term "antibody" refers to an immunoglobulin G (IgG) molecule comprising two heavy chains ("HC") and two light chains ("LC") inter-connected by disulfide bonds. Each heavy chain is comprised of a heavy chain variable region ("HCVR") and a heavy chain constant region ("CH"). Each light chain is comprised of a light chain variable region ("LCVR") and a light chain constant region ("CL"). Each HCVR and LCVR are further sub-dividable into regions of hypervariability, termed complementarity determining regions ("CDR"), interspersed with regions that are more conserved, termed framework regions ("FR"). Each HCVR and LCVR is composed of three CDRs and four FRs arranged from amino-terminus to carboxy-terminus in the following order: FR1, CDR1, FR2, CDR2, FR3, CDR3, FR4. The variable regions of each HC and LC contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

According to particular embodiments of aqueous pharmaceutical formulations provided herein, the antibodies are anti-IL17A antibodies. Interleukin 17A, or IL17A, as used herein refers to cytokines of the IL17 cytokine family (also known as cytotoxic T-lymphocyte-associated antigen 8 ("CTLA8")). IL17A cytokines exist as homodimeric complexes (e.g., IL17A/A) or as heterodimeric complexes in complex with another IL17 cytokine family member such as IL17F (e.g., IL17A/F). IL17A cytokines are believed to be produced primarily by effector T helper (Th17) cells and have been shown to induce secretion of pro-inflammatory cytokines such as IL-6, IL-8, IL-1 and TNF. The homodimeric complex form of IL17A, IL17A/A, has been shown to play a role in diseases such as psoriasis and psoriatic arthritis, both immune-related diseases associated with T cell dysregulation.

When referred to herein, such anti-IL17A antibodies are antibodies that specifically bind and antagonize human IL17A by way of specificity for the A subunit (e.g., the A subunit of IL17A/F or one or both of the A subunits of IL17A/A). According to specific embodiments of anti-IL17A antibodies, LCDR1 comprises the amino acid sequence of SEQ ID NO.1, LCDR2 comprises the amino acid sequence of SEQ ID NO.2, LCDR3 comprises the amino acid sequence of SEQ ID NO.3, HCDR1 comprises the amino acid sequence of SEQ ID NO.4, HCDR2 comprises the amino acid sequence of SEQ ID NO.5, and HCDR3 comprises the amino acid sequence of SEQ ID NO.6. According to some such embodiments, the LCVR comprises the amino acid sequence of SEQ ID NO.7 and the HCVR comprises the amino acid sequence of SEQ ID NO.8. In even more specific embodiments of such anti-IL17 antibodies, the LC comprises the amino acid sequence of SEQ ID NO.9 and the HC comprises the amino acid sequence of SEQ ID NO.10. An exemplary embodiment of an anti-IL17A antibody is ixekizumab, as described, for example, in U.S. Pat. No. 7,838,638. An additional example of an anti-IL17A antibody is secukinumab (marketed under the tradename COSENTYX®), as described, for example, in U.S. Pat. No. 7,807,155.

As may be used herein, the terms "about" or "approximately", when used in reference to a particular recited numerical value or range of values, means that the value may vary from the recited value by no more than 10% (e.g., +/−10%). For example, as used herein, the expression "about 100" includes 90 and 110 and all values in between (e.g., 91, 92, 93, 94, etc.).

As referred to herein, the terms "substantially free of" or "substantially devoid of" mean the presence of a given substance (e.g., ionic tonicity excipient) is below a limitation of detection for an assay used for detecting the presence of such substance.

The term "ionic tonicity excipient", as referred to herein, means an excipient that comprises an ionic compound (e.g., an electrolyte such as sodium chloride, potassium chloride, magnesium chloride, calcium chloride, arginine hydrochloride, or the like), which is distinct from the antibody and surfactant comprising an aqueous pharmaceutical formulation. An ionic tonicity excipient, as is known in the field, may be used to adjust the osmotic pressure of a pharmaceutical formulation. However (and as provided in the examples provided herein), adjustment of pH with HCl or NaOH, as necessary, following dissolution and mixing of the aqueous pharmaceutical formulation is not within the meaning of the term ionic tonicity excipient as used herein (as HCl or NaOH, added for pH adjustment are not acting in the formulation as an ionic tonicity excipient).

As referred to herein, the term L-amino acid excipients refers to L-amino acids which are added as either a part of a buffer (e.g., L-histidine in a histidine buffer; L-arginine in an arginine buffer, etc.) or as an excipient component of an aqueous pharmaceutical formulation (but does not refer to components of the therapeutic antibody).

As referred to interchangeably herein, the "visual analog scale" or "VAS", refers to an evaluation tool for assessing injection-associated pain experienced by a patient. VAS consists of a 100 mm contiguous scale, upon which a patient identifies their level of pain following injection. The VAS scoring extremes are "no pain at all" (e.g., 0) and "worst pain imaginable" (e.g., 100). Severity of pain may be categorized, according to the VAS tool, as mild pain (≤30 mm); moderate pain (>30 mm-≤70 mm) and severe pain (>70 mm). When referred to herein, "injection-associated pain" is in reference to acute pain experienced by a patient at the time of, or shortly after, injection of an aqueous pharmaceutical formulation. A desired property of a stable pharmaceutical formulation is being well tolerated by patients, for example, providing a therapeutically favorable level of injection-associated pain (e.g., a VAS score of <30 mm and/or <20 mm). As is known, the components, and concentrations and/or ratios thereof, of a pharmaceutical formulation may impact injection-associated pain experienced by the patient.

As used interchangeably herein, "treatment" and/or "treating" and/or "treat" are intended to refer to all processes wherein there may be a total elimination, slowing or delaying, reduction in severity or frequency (e.g., of flares or episodes), interruption or stopping of the progression of disease and/or symptoms thereof, but does not require a total elimination of all disease symptoms. Treatment includes administration of an aqueous pharmaceutical formulation of the present disclosure for treatment of a disease in a human that would benefit from at least one of the above-listed processes, including: (a) inhibiting further progression of disease symptoms and effects, i.e., arresting its development; (b) relieving the disease, i.e., causing an elimination or regression of disease, disease symptoms or complications thereof; and (c) preventing or reducing the frequency of disease episodes or flares. According to specific embodiments, the pharmaceutical formulations provided herein may be used in the treatment of at least one of RA, Ps, GenPs, AS, PA, PPP, HS or MM.

As used interchangeably herein, the term "patient," "subject" and "individual," refers to a human. Unless otherwise noted, the subject is further characterized as having, being at risk of developing, or experiencing symptoms of a disease that would benefit from administration of a pharmaceutical formulation disclosed herein.

As used interchangeably herein, an "effective amount" or "therapeutically effective amount" of a pharmaceutical formulation of the instant disclosure refers to an amount necessary (at dosages, frequency of administration and for periods of time for a particular means of administration) to achieve the desired therapeutic result. An effective amount of pharmaceutical formulation of the present disclosure may vary according to factors such as the disease state, age, sex, and weight of the subject and the ability of the pharmaceutical formulation of the present disclosure to elicit a desired response in the subject. An effective amount is also one in which any toxic or detrimental effects of the pharmaceutical formulation of the present disclosure are outweighed by the therapeutically beneficial effects.

The instant disclosure also relates to dose regimens for the treatment of a disease with a pharmaceutical formulation of the present disclosure. As referred to herein and as generally known in the art, the term "dose" refers to an amount of a pharmaceutical formulation that is administered to a subject. A "dose regimen" or "dosage regimen", as generally known in the field and as may be referred to interchangeably herein, includes a treatment schedule for administering a set (i.e., series or sequence) of doses to be administered to a patient over a period of time.

By way of example, a dose regimen of the present disclosure may include an initial dose of an aqueous pharmaceutical formulation (for example, comprising an anti-IL17A antibody) of the present disclosure administered to a patient on the first day of treatment (e.g., Day 0). An initial dose may be referred to herein as a "loading dose". Additionally, a dose regimen of the present disclosure may include an initial period of treatment, sometimes referred to herein as an "induction period", which follows the loading dose. During an induction period, for example, a patient may be administered a dose (or doses) comprising a specific concentration of a therapeutic antibody (e.g., anti-IL17A antibody), at a given frequency of administration (e.g., every day, every 2 weeks, every 4 weeks, etc.), for a given duration of time (e.g., 4, 12 or 16 weeks). Additionally, dose regimens of the present disclosure may include a period following the induction period, sometimes referred to herein as the "maintenance period", in which a patient is administered a dose comprising a specific concentration of the therapeutic antibody, at a given frequency of administration (e.g., every 2 or 4 weeks, etc.).

The aqueous pharmaceutical formulations of the present disclosure may be administered to a patient via parenteral administration. Parenteral administration, as understood in the medical field, refers to the injection of a dose into the body by a sterile syringe or some other drug delivery system including an autoinjector or an infusion pump. Exemplary drug delivery systems for use with the aqueous pharmaceutical formulations of the present disclosure are described in the following references, the disclosures of which are expressly incorporated herein by reference in their entirety: U.S. Patent Publication No. 2014/0054883 to Lanigan et al., filed Mar. 7, 2013 and entitled "Infusion Pump Assembly"; U.S. Pat. No. 7,291,132 to DeRuntz et al., filed Feb. 3, 2006 and entitled "Medication Dispensing Apparatus with Triple Screw Threads for Mechanical Advantage"; U.S. Pat. No. 7,517,334 to Jacobs et al., filed Sep. 18, 2006 and entitled "Medication Dispensing Apparatus with Spring-Driven Locking Feature Enabled by Administration of Final Dose";

and U.S. Pat. No. 8,734,394 to Adams et al., filed Aug. 24, 2012 and entitled "Automatic Injection Device with Delay Mechanism Including Dual Functioning Biasing Member." Parenteral routes include IM, SQ and IP routes of administration.

EXAMPLES

Exemplary Aqueous Pharmaceutical Formulation

TABLE 1

Exemplary Aqueous Pharmaceutical Formulation

|  | Concentration |
|---|---|
| anti-IL17A antibody* | 80 mg/mL |
| PS-80 | 0.03% w/v (0.3 mg/mL) |
| Sucrose | 234 mM (8% w/v) |
| pH | 5.7 |

*The anti-IL17A antibody comprises an HCVR of SEQ ID NO: 8 and an LCVR of SEQ ID NO: 7.

The manufacturing process for the anti-IL17A antibody pharmaceutical formulation presented in Table 1 may be accomplished by weighing an appropriate quantity of water (e.g., at a temperature of 20+/−5° C.) into a tared empty vessel of appropriate size. The appropriate quantity of sucrose is added and mixed. Polysorbate 80 is accurately weighed out in a glass container and an appropriate quantity of water at a temperature of 20+/−5° C. is added into the glass container to give the desired concentration and the solution is mixed. The entire content of the polysorbate 80 solution is added to the other excipients. The polysorbate 80 solution container is rinsed with water to ensure the entire contents are transferred. After addition of the polysorbate 80 solution, the solution is mixed. After dissolution and mixing has been completed, the pH of the solution is checked to be within 5.7+/−0.3; adjustment with HCl or NaOH solution is done if necessary. The excipient composition is passed through a filter (polyvinylidene fluoride [PVDF]) for bioburden reduction.

The anti-IL17A antibody, previously expressed in cells, purified, and concentrated, is mixed with an appropriate amount of the formulation excipient solution.

The pH of the solution is re-checked to be within 5.7+/−0.3. The pharmaceutical formulation is passed through a PVDF filter for bioburden reduction and may then be stored at 5° C.

Physical-Chemical Properties

Both physical and chemical stability is essential for a pharmaceutical formulation of a therapeutic antibody to allow storage and transportation (e.g., 1 year, 18 months, or 2 years) and preserve safety and efficacy. Exemplary evaluations to gauge the physical stability of a pharmaceutical formulation include solubility (phase-separation, gelation) assessments, molecular interactions (e.g., as measured by DLS), visual clarity (i.e., opalescence) characterization by turbidity assessment, and viscosity measurement. Additionally, chemical stability may be assessed using various analytical methods including size exclusion chromatography (SEC), cation exchange chromatography (CEX) HPLC, reduced and non-reduced capillary electrophoresis (CE-SDS R/NR) and particulate analysis. As demonstrated herein, the exemplified anti-IL17A antibody pharmaceutical formulation of Table 1 demonstrates chemical and physical stability as well as solubility for the highly concentrated therapeutic antibody, ixekizumab, which possesses an isoelectric point of ≥7.5, not compatible with formulation at neutral pH in solution.

Solubility Assessments

Sufficiently high solubility is essential for an aqueous pharmaceutical formulation. The aqueous pharmaceutical formulation must maintain the antibody in monomeric state, without high molecular weight (HMW) aggregation, at high concentration. Solubility of an anti-IL17A antibody, having an isoelectric point ≥8.0 (in solution), at high concentrations is analyzed under varying conditions.

Samples of each aqueous formulation provided in Table 2 are incubated at each of 5, 0 and −5 degrees Celsius (e.g., samples of each formulation may be incubated, in parallel, at 5, 0 and −5° C.) for one week. Following incubation samples are assessed for phase separation, gelation, turbidity and viscosity.

TABLE 2

Formulations

| Sample ID | Buffer | Non-Buffer Excipients | Anti-IL17A Antibody* Concentration | pH |
|---|---|---|---|---|
| Control (commercial formulation as described in U.S. Pat. No. 9,376,491) | 20 mM Citrate | 200 mM NaCl 0.03% PS-80 | 80 mg/mL | 5.7 |
| 1 (formulation of Table 1) | None | 234 mM sucrose 0.03% PS-80 | 80 mg/mL | 5.7 |
| 2 | 10 mM Citrate | 274 mM mannitol | 80 mg/mL | 5.7 |
| 3 | 10 mM Citrate | 274 mM mannitol 0.03% PS80 | 80 mg/mL | 5.7 |
| 4 | 10 mM Citrate | 234 mM sucrose 0.03% PS-80 | 80 mg/mL | 5.7 |
| 5 | 5 mM Citrate | 175 mM NaCl 0.03% PS80 | 80 mg/mL | 5.7 |
| 6 | 2.69 mM L-histidine 6.28 mM L-histidine hydrochloride monohydrate | 150 mM NaCl | 80 mg/mL | 6.5 |
| 7 | 2.69 mM L-histidine 6.28 mM L-histidine hydrochloride monohydrate | 150 mM NaCl 0.03% PS80 | 80 mg/mL | 6.5 |
| 8 | 2.69 mM L-histidine 6.28 mM L-histidine hydrochloride monohydrate | 150 mM NaCl 0.03% PS80 | 80 mg/mL | 5.7 |
| 9 | None | 130 mM NaCl | 80 mg/mL | 5.7 |
| 10 | None | 100 mM NaCl | 80 mg/mL | 5.7 |
| 11 | None | 65 mM NaCl | 50 mg/mL | 5.7 |
| 12 | 10 mM Citrate | None | 80 mg/mL | 5.7 |

*The anti-IL17A antibody comprises two HCVRs having the amino acid sequence of SEQ ID NO: 8 and two LCVRs having the amino acid sequence of SEQ ID NO: 7.
**In addition to the tested aqueous pharmaceutical formulations set forth in Table 2, an aqueous pharmaceutical formulation comprising 10 mM acetate buffer, 150 mM NaCl and 80 mg/mL of the anti-IL17A antibody, at pH 5.0, was assessed following incubation, wherein unacceptable levels of antibody clipping were observed by non-reduced CD-SDS.
***Additionally, as set forth in U.S. Pat. No. 9,376,491, unacceptable cloud point was observed for the anti-IL17A antibody with concentrations below either of 20 mM citrate buffer and 150 mM NaCl.

Phase Separation

As detailed in U.S. Pat. No. 9,376,491, the exemplified anti-IL17A antibody (comprising two LCVRs having the amino acid sequence of SEQ ID NO: 7 and two HCVRs having the amino acid sequences of SEQ ID NO: 8) has a propensity to phase separate in solution below 0 degrees Celsius (° C.). However, storage of drug product is at 5° C. and requires stability for periodic refrigeration temperature excursions below 0° C. As provided in U.S. Pat. No. 9,376,491, increasing citrate buffer and NaCl concentrations sufficiently lowers the temperature at which phase separation occurs. Injection-associated pain, however, has been reported to be associated with formulations comprising increased citrate buffer and NaCl concentrations and patients have reported injection-associated pain after injecting the commercial pharmaceutical formulation of ixekizumab.

Phase separation of formulations provided in Table 2 is assessed, following incubation at −5° C. for one week, by visual monitoring for signs of phase separation (e.g., the formation of a dense, protein rich layer at the bottom of the vial). Results are provided in Table 3.

Gelation

Events such as thermodynamic solid phase change (e.g., gelation) can occur at lower temperatures (5° C. or lower), negatively impacting stability. As detailed in U.S. Pat. No. 9,376,491, gelation has been observed with the exemplified anti-IL17A antibody at high concentrations at temperatures of 5° C. and below. U.S. Pat. No. 9,376,491 also shows that increasing citrate buffer and NaCl concentration sufficiently avoids gelation at lower temperatures. However, as noted, injection-associated pain has been reported to be associated with formulations comprising increased citrate buffer and NaCl concentrations and patients have reported injection-associated pain after injecting the commercial pharmaceutical formulation of ixekizumab.

Gelation assessment of formulations provided in Table 2 are provided in Table 3. Briefly, following incubation as described above, each vial is agitated (e.g., inverted and then returned upright) and then visually inspected for solidification or lack of liquid flow.

Turbidity

Turbidity (i.e., loss of transparency due to particulate matter suspension) is an inherent challenge for aqueous pharmaceutical formulations of therapeutic antibodies. The challenge is exasperated at high concentrations of antibodies and at lower temperatures, which can lead to the formulation failing visual inspection. Briefly, following incubation as described above, turbidity is assessed (measurements taken at ambient temperature) both visually (e.g., light-based method using purified water as a comparator) and by a nephlometer (HACH Turbidimeter, according to manufacturer instructions) yielding quantitative measurements (NTUs). Lower NTUs are desired; more specifically NTUs values of less than 50 are desired with a failure cut-off at 80 NTUs. Results are provided in Table 3.

Viscosity

An aqueous pharmaceutical formulation, to be acceptable for manufacturing, administration to and tolerability by patients must possess appropriate viscosity. Less viscous (at least <20 cP) aqueous solution is required in order to be subcutaneously delivered. Increased concentrations of therapeutic antibody present the challenge of increasing viscosity. It is known that pharmaceutical formulations with NaCl have decreased viscosity, but as noted, increasing NaCl concentration in a pharmaceutical formulation has been associated with injection-associated pain. Viscosity of formulation 1 and the control formulation of Table 2 is assessed following incubation at 20° C., by viscometer (Anton Paar AMVn Viscometer, according to manufacturer instructions) yielding centipoise (cP) measurements. Lower cP being desired, especially for example, <20 cP. Results are provided in Table 3.

TABLE 3

Solubility Assessment of the Formulations of Table 2

| Sample ID | Phase Separation Assessment | Gelation Assessment | Turbidity (NTUs) | Viscosity (cPs) |
|---|---|---|---|---|
| Control | No | No | 63 | 3 |
| 1 | No | No | 10 | 5 |
| 2 | Yes | ND | ND | ND |
| 3 | Yes | ND | ND | ND |
| 4 | Yes | ND | ND | ND |
| 5 | No | No | 85 | ND |
| 6 | No | Yes | ND | ND |
| 7 | No | Yes | ND | ND |
| 8 | No | No | 95 | ND |
| 9 | Yes | ND | ND | ND |
| 10 | Yes | ND | ND | ND |
| 11 | Yes | ND | ND | ND |
| 12 | Yes | ND | ND | ND |

As shown in Table 3, unacceptable phase separation or gelation was observed for all formulations lacking at least 150 mM NaCl (as well as the NaCl bufferless formulations), with the exception of formulation 1 which did not demonstrate phase separation. Phase separation results for formulation 1 are comparable to the control formulation (high citrate, high NaCl formulation). Also, unacceptable gelation was observed for formulations comprising histidine buffer and NaCl at pH 6.5. Formulation 1 did not demonstrate gelation and was comparable to the control formulation (high citrate, high NaCl formulation). Additionally, unacceptable turbidity was observed for both formulation 5 (citrate (5 mM), NaCl (175 mM)) and formulation 8 (histidine (9 mM) and NaCl (150 mM)). Formulation 1 demonstrated acceptable levels of turbidity and provided unexpected improved levels of turbidity compared to the control formulation (high citrate, high NaC1 formulation). Further, as shown, both formulation 1 and the control formulation exhibit acceptable and comparable viscosity.

Chemical Stability

Chemical stability is essential for the development of an aqueous pharmaceutical formulation both for allowing storage (i.e., sufficient shelf-life) and preserving safety and efficacy. Chemical stability comparing the control and formulation 1 (provided in Table 2) is assessed following an incubation period of four weeks at 25° C. or 40° C. in accelerated degradation studies. Change in % HMW aggregate is compared against % HMW aggregate at time 0.

In one assessment, the change in high molecular weight (HMW) aggregate in the formulations is assessed using size-exclusion chromatography (SEC) according to standard procedures. Results are provided in Table 4.

TABLE 4

Summary of change in % HMW aggregates measured by SEC

| Formulation # (of Table 2) | Change in % HMW aggregates 25° C. | Change in % HMW aggregates 40° C. |
|---|---|---|
| Control | 0.25 | 0.05 |
| 1 | 0.49 | 0.43 |

As shown, both the control formulation and formulation 1 of Table 2 demonstrate acceptable and comparable chemical stability in accelerated degradation studies. Additional accelerated chemical stability of the control and formulation 1 of Table 2 is studied using Cation Exchange (CEX) HPLC. Briefly, samples are incubated at 25° C. for four weeks. Following incubation, samples are analyzed for increase in total % acid variants (% AV) using CEX HPLC. Increase in total % acid variants (% AV) provides an indicator of degradation of the therapeutic antibody in the aqueous formulation. Results are provided in Table 5.

TABLE 5

Increase in % AV over 4 Weeks at 25° C.

| Formulation # (of Table 2) | Increase in % AV |
|---|---|
| Control | 2.0 |
| 1 | 2.3 |

As shown, both the control and formulation 1 of Table 2 demonstrate acceptable, and comparable, levels of chemical stability in the further accelerated degradation studies.

Multivariate Assessment of Formulation 1 of Table 2

As demonstrated herein, formulation 1 of Table 2 provides unexpected stability comparable to (or improved over) the control formulation of Table 2. A multivariate assessment of physical and chemical stability of formulation 1 of Table 2 is performed as set forth below.

Briefly, four variables (antibody concentration; pH; sucrose concentration; and PS-80 concentration) of formulation 1 of Table 2 are modified to assess physical and chemical stability response of each variable and/or interactions between the variables. Formulation 1 of Table 2 is set as the center point formulation for such experiment. Variant formulations are provided in Table 6.

TABLE 6

Variant Formulations

| Sample ID | Sucrose | PS-80** | Anti-IL17A* Antibody | pH |
|---|---|---|---|---|
| Center Point (formulation 1 of Table 2) | 234 mM | 0.03% | 80 mg/mL | 5.7 |
| 13 | 205 mM | 0.05% | 72 mg/mL | 5.2 |
| 14 | 205 mM | 0.005% | 72 mg/mL | 6.2 |
| 15 | 205 mM | 0.005% | 88 mg/mL | 5.2 |
| 16 | 205 mM | 0.05% | 88 mg/mL | 6.2 |
| 17 | 263 mM | 0.005% | 72 mg/mL | 5.2 |

TABLE 6-continued

Variant Formulations

| Sample ID | Sucrose | PS-80** | Anti-IL17A* Antibody | pH |
|---|---|---|---|---|
| 18 | 263 mM | 0.05% | 72 mg/mL | 6.2 |
| 19 | 263 mM | 0.05% | 88 mg/mL | 5.2 |
| 20 | 263 mM | 0.005% | 88 mg/mL | 6.2 |

*The anti-IL17A antibody comprises two HCVRs having the amino acid sequence of SEQ ID NO: 8 and two LCVRs having the amino acid sequence of SEQ ID NO: 7.
**Polysorbate tolerance for the ranges set forth in Table 6 are confirmed by accelerated freeze-thaw studies.

Each variant formulation is assessed for phase separation, gelation and turbidity according to procedures described above. This multivariate assessment provides identification of tolerance limitations for the assessed variables. No phase separation or gelation was observed and acceptable turbidity values were observed.

Long-term Stability Assessment

Long-term stability of an aqueous pharmaceutical formulation is required to demonstrate storage capability and sufficient shelf life (e.g., 1 year, 2 years or greater). Long-term stability of the center point formulation of Table 6 (which corresponds to the formulation provided in Table 1 and Formulation 1 of Table 2) is assessed following incubation of samples at: 5° C. for 1, 3 and 6 months; 25° C. for 1 and 3 months; and 35° C. for 1 and 3 months (assessment of sample prior to incubation is also performed).

Following incubation, samples are analyzed for percent monomer and percent high molecular weight (HMW) aggregate using size-exclusion chromatography (SEC) according to standard procedures. Results are provided in Table 7.

TABLE 7

Long Term Stability Assessment of Center Point Formulation

| Incubation Temp (° C.) | Incubation Period (months) | Monomer (%) | HMW Aggregate (%) |
|---|---|---|---|
| Control (pre-incubation) | NA | 98.61 | 1.27 |
| 5 | 1 | 98.83 | 1.10 |
| 5 | 3 | 98.57 | 1.39 |
| 5 | 6 | 98.61 | 1.27 |
| 5 | 12 | 98.67 | 1.28 |
| 25 | 1 | 98.59 | 1.32 |
| 25 | 3 | 98.01 | 1.85 |
| 35 | 1 | 97.93 | 1.70 |
| 35 | 3 | 95.54 | 3.30 |

As provided, the center point formulation of Table 6 demonstrates long-term stability for the therapeutic antibody, even under stressed conditions of extended periods at high temperatures.

In Vivo Tolerability Study

Assessment of injection-associated pain from subcutaneous injection of an aqueous pharmaceutical formulation of ixekizumab, at a high concentration (80 mg/mL), is performed according to a study in which subjects receive a SQ injection of one of Formulation A or B (as provided in Table 8), followed by a SQ injection of the other of Formulation A or B some period of time (e.g., 1, 5, 7, 10, 14, etc., days) later. Subjects are then assessed for injection-associated pain based on the VAS scale scoring at specified time points (e.g., within 1 minute (i.e., immediately after injection), within 10 minutes, within 1 hour, within 4 hours within 1 day) after each injection.

TABLE 8

Ixekizumab Pharmaceutical Formulation

| Formulation A (corresponds to center point formulation of Table 6) | | Formulation B (commercial formulation of Taltz ®) | |
|---|---|---|---|
| ixekizumab | 80 mg/mL | ixekizumab | 80 mg/mL |
| pH | 5.7 | pH | 5.7 |
| PS-80 | 0.3 mM | PS-80 | 0.03% w/v |
| sucrose | 80 mM | NaCl | 200 mM |
| | | Citrate buffer | 20 mM |

Accordingly, a single-dose, subject blinded, randomized, cross-over study is performed in which subjects are randomized into one of two treatment groups. Each treatment group receives subcutaneous injections of the pharmaceutical formulations comprising 80 mg/ml of ixekizumab, as set forth in Table 8, according to the following injection regimens.

Treatment group 1 receives a single dose of Formulation B, followed by a single dose of Formulation A seven days later. Treatment group 2 receives a single dose, by SQ injection, of Formulation A followed by a single dose, by SQ injection, of Formulation B fourteen days later. Injections are administered by medical personnel in the abdomen of the subject while the subject is in a sitting or reclining position. Subsequent injections may be alternated between abdominal quadrants. Assessment for injection-associated pain based on VAS scale scoring is performed immediately after each injection (e.g., within 1 min.) and at 10 minutes post injection. Results are provided in Tables 9 and 10 below.

TABLE 9

Injection-Associated Pain Comparability Data

| Formulation | VAS Score time post-injection (w/in 1 min.) | VAS Score time post-injection (10 mins.) |
|---|---|---|
| A (N = 63) | 3.52 | 0.68 |
| B (N = 61) | 25.21 | 5.15 |

As shown in Table 9, Formulation A provides a substantial decrease in VAS score over Formulation B (the commercially available formulation of Taltz®) both immediately after injection and at 10 minutes post-injection.

TABLE 10

Patient Tolerability Analysis

| VAS Score | Formulation A time post-injection (w/in 1 min.) | Formulation B time post-injection (w/in 1 min.) |
|---|---|---|
| No pain (VAS = 0) | 26 (of 63 patients): 41.3% | 5 (of 61 patients): 8.2% |
| Mild Pain (VAS ≤ 30) | 36 (of 63 patients): 57.1% | 36 (of 61 patients): 59.0% |
| Moderate-to-Severe Pain (VAS > 30) | 1 (of 63 patients): 1.6% | 20 (of 61 patients): 32.8% |

As shown in Table 10, Formulation A provides a substantial improvement in patients experiencing no injection-associated pain immediately post-injection as well as a substantial benefit in the reduction of patients experiencing moderate-to-severe injection-associated pain immediately post-injection over Formulation B (the commercially available formulation of Taltz®).

In Vivo Pharmacokinetic Analysis

Pharmacokinetic analysis of an aqueous pharmaceutical formulation of ixekizumab may be performed according to a study in which subjects receive a SQ injection of one of Formulation A or B (as provided in Table 8). Subjects are then assessed for pharmacokinetic analysis at various time points (e.g., prior to SQ injection and then post-SQ injection such as 1-24 hrs., 1-90 days post-injection).

Accordingly, a single-dose, subject blinded, randomized, parallel design study is performed in which, on day 1, subjects are randomized into one of two treatment groups. Prior to receiving a treatment (e.g., day 1, pre-dose) a pre-dose sample from patients of both treatment groups is taken for pharmacokinetic property assessment. On Day 1, treatment group 1 receives a single, SQ injection of Formulation A and treatment group 2 receives a single, subcutaneous injection of Formulation B (as described in Table 8). Injections may be administered by medical personnel in the abdomen of the subjects. Post-dosing, samples are taken on study days 3, 5 (±1 day), 8 (±1 day), 11 (±1 day), 15 (±2 days), 22 (±2 days), 29 (±2 days), 43 (±2 days), 57 (±3 days), 71 (±3 days) and 85 (±3 days) to assess pharmacokinetic parameters including Cmax (maximum observed drug concentration), AUC[0-∞] (area under the concentrations versus time curve from time zero to infinity), AUC[0-$t_{last}$] (area under the concentrations versus time curve from time zero on study Day 1 to time of last measurable concentration), and Tmax (time of the maximum observed drug concentration). Results are provided in Table 11.

TABLE 11

In Vivo Pharmacokinetic Analysis

| Formulation | $P_K$ Parameter | Value (geometric least squares mean) | Ratio (Form. A/ Form B) |
|---|---|---|---|
| Formulation A (N = 33) | AUC[0-∞] (ug*day/mL) | 159 | 1.05 |
| Formulation B (N = 32) | | 152 | |
| Formulation A (N = 33) | AUC[0-$t_{last}$] (ug*day/mL) | 153 | 1.04 |
| Formulation B (N = 32) | | 146 | |
| Formulation A (N = 33) | Cmax (ug/mL) | 6.29 | 1.00 |
| Formulation B (N = 33) | | 6.31 | |
| Formulation A (N = 33) | Tmax (days) | 4.09 | (median of differences) 0 |
| Formulation B (N = 33) | | 3.95 | |

As shown in Table 11, Formulation A demonstrates comparable PK parameters to Formulation B (the commercially available formulation of Taltz®). Also, no severe adverse events were reported for either formulation and overall safety is consistent and comparable to Formulation B.

Target Neutralization Assessment

Following incubation of samples of Formulation A at 5° C. for 1, 6 and 12 months; 25° C. for 1 month; and 35° C.

for 1 month, potency of Formulation A is assessed in comparison to Formulation B (of Table 8) by way of a cell-based bioassay. Briefly, murine osteoblast cell line MC3T3-E1, which endogenously expresses IL-17A receptor and stably expresses firefly luciferase gene, is cultured such that when IL-17A is present transcription of luciferase is induced at levels proportional to IL-17A activity. Previously incubated samples of Formulation A and B are introduced to culture wells of the cell-based bioassay, respectively, and following measurement of luciferase expression, inhibition dose curves are generated. Data is analyzed using a four parameter logistic curve fit. Relative potency is determined by calculating the ratio of the $EC_{50}$ for Formulation A in comparison to the $EC_{50}$ of Formulation B (e.g., the reference standard). Results are provided in Table 12.

TABLE 12

Relative Potency Assessment of Formulation A (% relative to Formulation B)

| Incubation Period (Months) | Incubation Temp. (° C.) | | |
|---|---|---|---|
| | 5° C. | 25° C. | 35° C. |
| 1 | 101% | 98% | 101% |
| 6 | 103% | ND | ND |
| 12 | 98% | ND | ND |

As shown in Table 12, Formulation A demonstrates levels of target neutralization comparable to Formulation B (the commercially available formulation of Taltz®) after extended periods of storage and under stressed conditions.

Sequences
(LCDR1 of Exemplary anti-IL17A antibody)
SEQ ID NO: 1
RSSRSLVHSRGNTYLH (LCDR2 of Exemplary anti-IL17A antibody)
SEQ ID NO: 2
KVSNRFI (LCDR3 of Exemplary anti-IL17A antibody)
SEQ ID NO: 3
SQSTHLPFT (HCDR1 of Exemplary anti-IL17A antibody)
SEQ ID NO: 4
GYSFTDYHIH (HCDR2 of Exemplary anti-IL17A antibody)
SEQ ID NO: 5
VINPMYGTTDYNQRFKG (HCDR3 of Exemplary anti-IL17A antibody)
SEQ ID NO: 6
YDYFTGTGVY (LCVR of Exemplary anti-IL17A antibody)
SEQ ID NO: 7
DIVMTQTPLSLSVTPGQPASISCRSSRSLVHSRGNTYLHWYLQKPGQSP
QLLIYV SNRFIGVPDRFSGSGSGTDFTLKISRVEAEDVGVYYCSQSTH
LPFTFGQGTKLEIK (HCVR of Exemplary anti-IL17A antibody)
SEQ ID NO: 8
QVQLVQSGAEVKKPGSSVKVSCKASGYSFTDYHIHWVRQAPGQGLEWMG
VINPMYGTTDYNQRFKGRVTITADESTSTAYMELSSLRSEDTAVYYCAR
YDYFTGTGVYWGQGTLVTVSS (light chain of Exemplary anti-IL17A antibody)
SEQ ID NO: 9
DIVMTQTPLSLSVTPGQPASISCRSSRSLVHSRGNTYLHWYLQKPGQSP
QLLIYKVSNRFIGVPDRFSGSGSGTDFTLKISRVEAEDVGVYYCSQSTH
LPFTFGQGTKLEIKRTVAAPSVFIFPPSDEQLKSGTASVVCLLNNFYPR
EAKVQWKVDNALQSGNSQESVTEQDSKDSTYSLSSTLTLSKADYEKHKV
YACEVTHQGLSSPVTKSFNRGEC (heavy chain of Exemplary anti-IL17A antibody)
SEQ ID NO: 10
QVQLVQSGAEVKKPGSSVKVSCKASGYSFTDYHIHWVRQAPGQGLEWMG
VINPMYGTTDYNQRFKGRVTITADESTSTAYMELSSLRSEDTAVYYCAR
YDYFTGTGVYWGQGTLVTVSSASTKGPSVFPLAPCSRSTSESTAALGCL
VKDYFPEPVTVSWNSGALTSGVHTFPAVLQSSGLYSLSSVVTVPSSSLG
TKTYTCNVDHKPSNTKVDKRVESKYGPPCPPCPAPEFLGGPSVFLFPPK
PKDTLMISRTPEVTCVVVDVSQEDPEVQFNWYVDGVEVHNAKTKPREEQ
FNSTYRVVSVLTVLHQDWLNGKEYKCKVSNKGLPSSIEKTISKAKGQPR
EPQVYTLPPSQEEMTKNQVSLTCLVKGFYPSDIAVEWESNGQPENNYKT
TPPVLDSDGSFFLYSRLTVDKSRWQEGNVFSCSVMHEALHNHYTQKSLS
LSLG

We claim:

1. A bufferless aqueous pharmaceutical formulation comprising:
   (i) an anti-IL-17A antibody at a concentration of 80 mg/mL+/−10%;
   (ii) sucrose in a concentration of 234 mM+/−10%; and
   (iv) a surfactant in a concentration of between 0.005% w/v+/−10% to 0.05% w/v+/−10%,
   wherein, the pharmaceutical formulation is an aqueous solution at a pH between 5.2 to 6.5 and the anti-IL17A antibody comprises a light chain variable region (LCVR) and a heavy chain variable region (HCVR), wherein the LCVR comprises complementarity determining regions (CDRs) LCDR1, LCDR2, and LCDR3 and the HCVR comprises CDRs HCDR1, HCDR2, and HCDR3, wherein:
   LCDR1 comprises the amino acid sequence of SEQ ID NO. 1,
   LCDR2 comprises the amino acid sequence of SEQ ID NO. 2,
   LCDR3 comprises the amino acid sequence of SEQ ID NO. 3,
   HCDR1 comprises the amino acid sequence of SEQ ID NO. 4,
   HCDR2 comprises the amino acid sequence of SEQ ID NO. 5, and
   HCDR3 comprises the amino acid sequence of SEQ ID NO. 6.

2. The pharmaceutical formulation of claim 1, wherein the surfactant is polysorbate 20 or polysorbate 80.

3. The pharmaceutical formulation of claim 2, wherein the surfactant is polysorbate 80.

4. The pharmaceutical formulation of claim 1, wherein the pharmaceutical formulation is substantially free of ionic tonicity excipient.

5. The pharmaceutical formulation of claim 1, wherein the pharmaceutical formulation is substantially free of L-amino acid excipients.

6. The pharmaceutical formulation of claim 1, wherein the LCVR comprises the amino acid sequence of SEQ ID NO. 7 and the HCVR comprises the amino acid sequence of SEQ ID NO. 8.

7. The pharmaceutical formulation of claim 6, wherein anti-IL17A antibody comprises a light chain (LC) and a heavy chain (HC), wherein the LC comprises the amino acid sequence of SEQ ID NO. 9 and the HC comprises the amino acid sequence of SEQ ID NO. 10.

8. The pharmaceutical formulation of claim 7, wherein the anti-IL17A antibody is ixekizumab.

9. The pharmaceutical formulation of claim 1, wherein the surfactant is polysorbate 80, the pharmaceutical formulation is substantially free of ionic tonicity excipient and is substantially free of L-amino acid excipients, and wherein the LCVR comprises the amino acid sequence of SEQ ID NO. 7 and the HCVR comprises the amino acid sequence of SEQ ID NO. 8.

* * * * *

UNITED STATES PATENT AND TRADEMARK OFFICE
CERTIFICATE OF CORRECTION

| | |
|---|---|
| PATENT NO. | : 11,634,485 B2 |
| APPLICATION NO. | : 16/787254 |
| DATED | : April 25, 2023 |
| INVENTOR(S) | : Vincent John Corvari and Karthik Pisupati |

It is certified that error appears in the above-identified patent and that said Letters Patent is hereby corrected as shown below:

In the Claims

In Claim 1 found at Column 27, Line 43, delete "(iv)" and insert --(iii)--.

Signed and Sealed this
Fourth Day of July, 2023

Katherine Kelly Vidal
*Director of the United States Patent and Trademark Office*

SEQUENCE LISTING

<160> NUMBER OF SEQ ID NOS: 10

<210> SEQ ID NO 1
<211> LENGTH: 16
<212> TYPE: PRT
<213> ORGANISM: Artificial Sequence
<220> FEATURE:
<223> OTHER INFORMATION: LCDR1

<400> SEQUENCE: 1

Arg Ser Ser Arg Ser Leu Val His Ser Arg Gly Asn Thr Tyr Leu His
1               5                   10                  15

<210> SEQ ID NO 2

```
<211> LENGTH: 7
<212> TYPE: PRT
<213> ORGANISM: Artificial Sequence
<220> FEATURE:
<223> OTHER INFORMATION: LCDR2

<400> SEQUENCE: 2

Lys Val Ser Asn Arg Phe Ile
1               5

<210> SEQ ID NO 3
<211> LENGTH: 9
<212> TYPE: PRT
<213> ORGANISM: Artificial Sequence
<220> FEATURE:
<223> OTHER INFORMATION: LCDR3

<400> SEQUENCE: 3

Ser Gln Ser Thr His Leu Pro Phe Thr
1               5

<210> SEQ ID NO 4
<211> LENGTH: 10
<212> TYPE: PRT
<213> ORGANISM: Artificial Sequence
<220> FEATURE:
<223> OTHER INFORMATION: HCDR1

<400> SEQUENCE: 4

Gly Tyr Ser Phe Thr Asp Tyr His Ile His
1               5                   10

<210> SEQ ID NO 5
<211> LENGTH: 17
<212> TYPE: PRT
<213> ORGANISM: Artificial Sequence
<220> FEATURE:
<223> OTHER INFORMATION: HCDR2

<400> SEQUENCE: 5

Val Ile Asn Pro Met Tyr Gly Thr Thr Asp Tyr Asn Gln Arg Phe Lys
1               5                   10                  15

Gly

<210> SEQ ID NO 6
<211> LENGTH: 10
<212> TYPE: PRT
<213> ORGANISM: Artificial Sequence
<220> FEATURE:
<223> OTHER INFORMATION: HCDR3

<400> SEQUENCE: 6

Tyr Asp Tyr Phe Thr Gly Thr Gly Val Tyr
1               5                   10

<210> SEQ ID NO 7
<211> LENGTH: 112
<212> TYPE: PRT
<213> ORGANISM: Artificial Sequence
<220> FEATURE:
<223> OTHER INFORMATION: LCVR

<400> SEQUENCE: 7

Asp Ile Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
```

```
                20                  25                  30
Arg Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ile Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Leu Pro Phe Thr Phe Gly Gln Gly Thr Lys Leu Glu Ile Lys
            100                 105                 110
```

<210> SEQ ID NO 8
<211> LENGTH: 119
<212> TYPE: PRT
<213> ORGANISM: Artificial Sequence
<220> FEATURE:
<223> OTHER INFORMATION: HCVR

<400> SEQUENCE: 8

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
        35                  40                  45

Gly Val Ile Asn Pro Met Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Phe Thr Gly Thr Gly Val Tyr Trp Gly Gln Gly
            100                 105                 110

Thr Leu Val Thr Val Ser Ser
        115
```

<210> SEQ ID NO 9
<211> LENGTH: 219
<212> TYPE: PRT
<213> ORGANISM: Artificial Sequence
<220> FEATURE:
<223> OTHER INFORMATION: light chain

<400> SEQUENCE: 9

```
Asp Ile Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ile Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95
```

```
Thr His Leu Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
            210                 215
```

<210> SEQ ID NO 10
<211> LENGTH: 445
<212> TYPE: PRT
<213> ORGANISM: Artificial Sequence
<220> FEATURE:
<223> OTHER INFORMATION: heavy chain

<400> SEQUENCE: 10

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
        35                  40                  45

Gly Val Ile Asn Pro Met Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Phe Thr Gly Thr Gly Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240
```

```
Leu Phe Pro Pro Lys Pro Lys Asp Thr Leu Met Ile Ser Arg Thr Pro
            245             250                 255

Glu Val Thr Cys Val Val Val Asp Val Ser Gln Glu Asp Pro Glu Val
            260             265                 270

Gln Phe Asn Trp Tyr Val Asp Gly Val Glu Val His Asn Ala Lys Thr
            275             280                 285

Lys Pro Arg Glu Glu Gln Phe Asn Ser Thr Tyr Arg Val Val Ser Val
            290             295                 300

Leu Thr Val Leu His Gln Asp Trp Leu Asn Gly Lys Glu Tyr Lys Cys
305             310              315                 320

Lys Val Ser Asn Lys Gly Leu Pro Ser Ser Ile Glu Lys Thr Ile Ser
            325             330                 335

Lys Ala Lys Gly Gln Pro Arg Glu Pro Gln Val Tyr Thr Leu Pro Pro
            340             345                 350

Ser Gln Glu Glu Met Thr Lys Asn Gln Val Ser Leu Thr Cys Leu Val
            355             360                 365

Lys Gly Phe Tyr Pro Ser Asp Ile Ala Val Glu Trp Glu Ser Asn Gly
            370             375                 380

Gln Pro Glu Asn Asn Tyr Lys Thr Thr Pro Pro Val Leu Asp Ser Asp
385             390             395                 400

Gly Ser Phe Phe Leu Tyr Ser Arg Leu Thr Val Asp Lys Ser Arg Trp
                405              410                415

Gln Glu Gly Asn Val Phe Ser Cys Ser Val Met His Glu Ala Leu His
            420             425                 430

Asn His Tyr Thr Gln Lys Ser Leu Ser Leu Ser Leu Gly
            435             440             445
```